United States Patent
Fung et al.

(10) Patent No.: US 7,618,657 B2
(45) Date of Patent: Nov. 17, 2009

(54) **ACTIVE INGREDIENTS PREPARATION AND SINGLE COMPOUND PURIFICATION FROM TRADITIONAL CHINESE HERBAL MEDICINE *FRUCTUS TRICHOSANTHIS* AND USES THEREOF**

(75) Inventors: Ming Chiu Fung, Hong Kong (CN); Hong Tao Xing, Hong Kong (CN)

(73) Assignee: Ultra Biotech Limited, Hong Kong (CN)

( * ) Notice: Subject to any disclaimer, the term of this patent is extended or adjusted under 35 U.S.C. 154(b) by 118 days.

(21) Appl. No.: 10/783,619

(22) Filed: Feb. 20, 2004

(65) Prior Publication Data

US 2004/0180100 A1 Sep. 16, 2004

Related U.S. Application Data

(60) Provisional application No. 60/448,935, filed on Feb. 21, 2003.

(51) Int. Cl.
*A01N 65/00* (2009.01)
*A61K 36/428* (2006.01)
*A61K 47/00* (2006.01)
*A61K 36/00* (2006.01)

(52) U.S. Cl. .................. 424/725; 514/783; 424/773; 424/779; 424/774; 424/778; 424/777; 424/776

(58) Field of Classification Search .................. None
See application file for complete search history.

(56) References Cited

U.S. PATENT DOCUMENTS 5,910,307 A * 6/1999 Kwak et al. .................. 424/745

6,231,880 B1 5/2001 Perrine

FOREIGN PATENT DOCUMENTS

| JP | 62108844 | * | 5/1987 |
| JP | 62108844 | A | 5/1987 |
| JP | 62108844 | A * | 5/1987 |
| KR | 2001035445 | A | 5/2001 |
| KR | 2001-0106527 | | 12/2001 |
| KR | 2001106527 | * | 12/2001 |

OTHER PUBLICATIONS

Ozaki et al., Antiinflammatory effect of *Trichosanthes kirilowii* Maxim, and its effective parts.Biological & pharmaceutical bulletin, (Aug. 1996) vol. 19, No. 8, pp. 1046-1048.*

Ozaki et al., Antiinflammatory effect of *Trichosanthes kirilowii* Maxim. and its effective parts. Biological & pharmaceutical bulletin, 19 (8): 1046-8, 1996.*

Oh et al., Cucurbitacins from *Trichosanthes kirilowii* as the inhibitory components on tyrosinase activity and melanin synthesis of B16/F10 melanoma cells. Planta Med 68: 832-833, 2002.*

International Search Report for the PCT/International Application, No. PCT/CN2004/000139, dated Jun. 17, 2004, 3 pages.

Ozaki et al., "Antiinflammatory effect of *Trichosanthes kirilowii* Maxim, and its effective parts," Biol Pharm Bull. Aug. 1996;19(8):1046-8.

* cited by examiner

*Primary Examiner*—Michele Flood
*Assistant Examiner*—Qiuwen Mi
(74) *Attorney, Agent, or Firm*—George C. Wang; Wilkinson & Grist (57) ABSTRACT

Disclosed are an extract from traditional Chinese herbal medicine *Trichosanthes* with the activity of increasing globin gene expression and a composition comprising the extract. A method for preparing the extract and use thereof in treating disorders related to globing gene expression is also provided.

17 Claims, 5 Drawing Sheets

Dot/lines show Means
Error Bars show 95.0% CI of Mean

ACTIVE INGREDIENTS PREPARATION AND SINGLE COMPOUND PURIFICATION FROM TRADITIONAL CHINESE HERBAL MEDICINE *FRUCTUS TRICHOSANTHIS* AND USES THEREOF

RELATED APPLICATIONS

The present application claims the benefit of U.S. provisional application Ser. No. 60/448,935 filed on Feb. 21, 2003, entitled the same, now pending, which is explicitly incorporated herein by reference in its entirety.

BACKGROUND OF THE INVENTION

1. Field of the Invention

The present invention relates to antianemia ingredients extracted from traditional Chinese herbal medicine *Trichosanthes*, which comprise a single compound with the activity of increasing globin gene expression. This invention also relates to methods of preparing the ingredients and purifying the compound, and uses thereof.

2. Description of the Related Art

The hereditary hemoglobinopathies such as sickle cell anemia and thalassemias are among the most prevalent serious genetic disorders affecting human populations and represent a major health burden worldwide. Even nowadays, blood transfusions remain the major means to ameliorate the clinical anemia syndromes although they are only of temporary benefit. Hypertransfusion induced iron overload requires effective iron chelating therapy to improve growth and prolong survival in patients. Bone marrow transplantation can cure the disease but has not been widely performed because of risk, expense, the need for an HLA compatible donor and poor acceptance by families and patients.

Recently, the search for treatment aimed at reduction of globin chain imbalance in patients with thalassemia has focused on the pharmacologic manipulation of fetal hemoglobin ($\alpha_2\gamma_2$; HbF). The switch from fetal hemoglobin to adult hemoglobin ($\alpha_2\beta_2$; HbA) usually proceeds within six months after parturition, which unfortunately also proceeds on schedule in patients with hemoglobinopathies. However, in the majority of these individuals, the upstream $\gamma$ globin genes are intact and fully functional, and if these could be reactivated, functional hemoglobin synthesis could be maintained during adulthood, ameliorating the severity of the disease (Atweh, G. F., and D. Loukopoulos, 2001, Pharmacological induction of fetal hemoglobin in sickle cell disease and beta-thalassemia, Semin Hematol, 38: 367-73). This is suggested by observations of the mild phenotype of individuals with co-inheritance of homozygous $\beta$-thalassemia and hereditary persistence of fetal hemoglobin (HPFH), and by those patients with homozygous $\beta^0$-thalassemia who synthesize no adult hemoglobin, but in whom a reduced requirement for transfusions is observed in the presence of increased concentrations of fetal hemoglobin.

The first group of compounds discovered having HbF reactivation activity are cytotoxic drugs. 5-azacytidine was initially found, in experimental animals, impressing cellular control of fetal hemoglobin in the adult (DeSimone, J., P. Heller, L. Hall and D. Zwiers, 1982, 5-Azacytidine stimulates fetal hemoglobin synthesis in anemic baboons, Proc Natl Acad Sci USA, 79: 4428-31). Later baboons treated with cytotoxic doses of arabinosylcytosine (ara-C) responded with striking elevations of F-reticulocytes (Papayannopoulou, T., A. Torrealba de Ron, R. Veith, G. Knitter and G. Stamatoyannopoulos, 1984, Arabinosylcytosine induces fetal hemoglobin in baboons by perturbing erythroid cell differentiation kinetics, Science, 224: 617-9). Induction of $\gamma$-globin also occurred in monkeys or baboons treated with hydroxyurea (Letvin, N. L., D. C. Linch, G. P. Beardsley, K. W. McIntyre and D. G. Nathan, 1984, Augmentation of fetal-hemoglobin production in anemic monkeys by hydroxyurea, N Engl J Med, 310: 869-73). Vinblastine, an M stage-specific agent that arrests cells in mitosis, also produces perturbations of erythropoiesis and stimulates HbF synthesis in baboons (Veith, R., T. Papayannopoulou, S. Kurachi and G. Stamatoyannopoulos, 1985, Treatment of baboon with vinblastine: insights into the mechanisms of pharmacologic stimulation of Hb F in the adult, Blood, 66: 456-9). Following these studies, hydroxyurea was used for induction of HbF in humans and later became the first and only drugs approved by the Food and Drug Administration (FDA) for the treatment of hemoglobinopathies. However, the pharmacologic induction of HbF through the mechanism of late progenitor cell cytotoxicity seems to reach a dead end in drug discovery. It is unlikely that a cytotoxic compound better than hydroxyurea could be found.

The second group of compounds owning to HbF reactivation activity was short chain fatty acids. Initially, the seminal observation led to the discovery of $\gamma$-aminobutyric acid, which is acting as a fetal hemoglobin inducer (Perrine, S. P., B. A. Miller, M. F. Greene, R. A. Cohen, N. Cook et al., 1987, Butryic acid analogues augment gamma globin gene expression in neonatal erythroid progenitors, Biochem Biophys Res Commun, 148: 694-700). Subsequent studies showed that butyrate stimulated globin production in adult baboons (Constantoulakis, P., T. Papayannopoulou and G. Stamatoyannopoulos, 1988, alpha-Amino-N-butyric acid stimulates fetal hemoglobin in the adult, Blood, 72: 1961-7), and it induced y globin in erythroid progenitors in adult animals or patients with sickle cell anemia (Perrine, S. P., B. A. Miller, D. V. Faller, R. A. Cohen, E. P. Vichinsky et al., 1989, Sodium butyrate enhances fetal globin gene expression in erythroid progenitors of patients with Hb SS and beta thalassemia, Blood, 74: 454-9). Derivatives of short chain fatty acids such as phenylbutyrate (Dover, G. J., S. Brusilow and S. Charache, 1994, Induction of fetal hemoglobin production in subject,s with sickle cell anemia by oral sodium phenylbutyrate, Blood, 84: 339-43) and valproic acid (Liakopoulou, E., C. A. Blau, Q. Li, B. Josephson, J. A. Wolf et al., 1995, Stimulation of fetal hemoglobin production by short chain fatty acids, Blood, 86: 3227-35) also induce HbF in vivo. Since there exist a very large number of short chain fatty acid analogs or derivatives that are potential inducers of HbF, there are ample opportunities for discovering HbF inducers that are more potent than butyrate. Phenylacetic and phenylalkyl acids (Torkelson, S., B. White, D. V. Faller, K. Phipps, C. Pantazis et al., 1996, Erythroid progenitor proliferation is stimulated by phenoxyacetic and phenylalkyl acids, Blood Cells Mol Dis, 22: 150-8), which were discovered during following studies, belonged to such examples. Presently, the use of butyrate or its analogs in sickle cell anemia and $\beta$-thalassemia remains experimental and cannot be recommended for treatment outside of clinical trials.

Clinical trials aimed at reactivation of fetal hemoglobin synthesis in sickle cell anemia and $\beta$-thalassemia have included short term and long term administration of 5-azacytidine, hydroxyurea, recombinant human erythropoietin, and butyric acid analogs, as well as combinations of these agents. However, varying drawbacks contraindicate the long term use of such agents or therapies. For example, although the hydroxyurea stimulates fetal hemoglobin production and clinically reduces sickling crisis, it is potentially limited by myelotoxicity and the risk of carcinogenesis. Potential long term carcinogenicity also exists in 5-azacytidine-based therapies. Feasible clinical treatments for these diseases remain scarce. Erythropoietin-based therapies have not proved consistent among a range of patient populations. The short half-lives of butyric acid in vivo have been viewed as a potential obstacle in clinical settings.

Still, notable efforts have been made in discovery and developing new drugs for the treatment of sickle cell anemia and β-thalassemia. In the past decades, some progress has also been made in the pharmacological management of sickle cell anemia and thalassemia.

WO 9,712,855 (Tung Roger D.) describes butyrate prodrugs derived from lactic acid for increasing gamma globin and fetal hemoglobin in a patient. The compounds disclosed in the application are particularly effective in treating beta-hemoglobinopathies, including sickle cell syndromes and beta-thalassemia syndromes.

U.S. Pat. No. 6,372,213 (Um, et al.) provides a method of treatment of sickle cell anemia or thalassemia with protein C. The patent provides a needed therapy for potentially serious and debilitating disorders while avoiding complications such as bleeding tendency, toxicity and general side effects of currently available anti-coagulant agents.

U.S. Pat. No. 6,312,707 (Markov, et al.) describes fructose-1,6-diphosphate (FDP) has been shown, in double-blinded controlled clinical trials on patients with sickle cell anemia, to substantially reduce the pain suffered by such patients during the recurrent ischemic crises that are caused by red blood cell sickling.

U.S. Pat. No. 6,231,880 (Perrine) describes a number of compositions for pulsed administration to treat human blood disorders such as sickle cell anemia or thalassemia. The compositions contain chemical compounds that stimulate the expression of fetal hemoglobin and stimulate the proliferation of red blood cells, white blood cells and platelets in patients and ex vivo for reconstitution of hematopoiesis in vivo.

U.S. Pat. No. 6,028,103 (Brugnara, et al.) discloses that triaryl methane compounds or analogues are useful as efficacious drugs in the treatment of sickle cell disease and diseases characterized by unwanted or abnormal cell proliferation. The compounds inhibit mammalian cell proliferation, inhibit the Gardos channel of erythrocytes, reduce sickle erythrocyte dehydration and delay the occurrence of erythrocyte sickling or deformation.

U.S. Pat. No. 5,945,407 (Bemis, et al.) describes uses of butyrate esters of threitol in pharmaceutically increasing fetal hemoglobin and gamma globin in a patient, and particularly in treating beta-hemoglobinopathies, such as sickle cell syndromes and beta-thalassemia syndromes.

U.S. Pat. No. 5,753,632 (Schmidt, et al.) describes the use of colloidal silica for the treatment of sickle-cell anemia, malaria and exogenously induced leucopenias, which leads to a significant improvement in the condition of the patients.

U.S. Pat. No. 5,665,392 (Kumar, et al.) describes a pharmaceutical formulation useful for treating patients suffering from thalassemia, which comprises powder of Anemonin Pretensis in an amount in the range of 0.02 to 0.12 wt % of the formulation, quinine sulphate in an amount in the range of 0.0005 to 0.003 wt % of the formulation, distilled or demineralised water in an amount in the range of 0 to 40 wt % of the formulation and, ethanol in an amount in the range of 99.88 to 60 wt % of the formulation; and a process for preparing the formulation by mixing the above ingredients.

U.S. Pat. No. 5,447,720 (Fadulu) describes a composition extracted from alfalfa and other certain plant materials for the treatment of hemoglobinopathies. The plant material is first extracted with 1,1,1-trichloroethane and a hydroxide base, followed by extraction with hexane. The polar acidic compounds present in alfalfa and other plant materials selectively dissolve in the hexane phase and exhibit good antisickling activity in vitro. Further, these active compounds which comprise the inventive extract are effective in vivo by significantly alleviating the many clinical manifestations of sickle cell anemia and thalassemia patients.

EP 0,627,220 (Hayhurst Walter) describes pharmaceutical compositions containing butyric acid derivatives, particularly isobutyramide, are advantageously indicated for the therapy of thalassemia when compared with known formulations.

EP 0,617,966 (Perrine Susan P.) describes a method for inhibiting the gamma-globin to beta-globin switching in subjects afflicted with beta-globin disorders. It ameliorates the clinical symptoms of sickle cell disease or beta-thalassemia by introducing activin or inhibin into the subject prior to natural completion of the switching process.

Although these efforts lead advances in developing new drugs for the treatment of hemoglobinopathies, most of them are still under further investigation, as still far from practical use. It is apparent that the present treatment of the sickle cell anemia and β-thalassemia is not ideal. Limited effectiveness, risks, expenses, and difficulties in compliance characterize most of the therapies currently available. Accordingly, it is urgent to develop alternatives having advantages over the prior art, and avoiding the disadvantages of those disclosed in the prior art, while providing effective therapy for those target diseases.

SUMMARY OF THE INVENTION

Accordingly, an object of the present invention is to provide an extract from a plant of *Trichosanthes* having an activity for increasing hemoglobin expression level, reactivating fetal or adult hemoglobin, inducing γ-globin, stimulating cell differentiation, inhibiting malignant cell proliferation, or treating a hemoglobinopathy or a malignant disease in a subject.

Another object of the present invention is to provide a method for preparing an extract of a plant of *Trichosanthes* having an activity for increasing hemoglobin expression level, reactivating fetal or adult hemoglobin, inducing γ-globin, stimulating cell differentiation, inhibiting malignant cell proliferation, or treating a hemoglobinopathy or a malignant disease in an subject.

Still another object of the present invention is to provide a pharmaceutical composition for increasing hemoglobin expression level, reactivating fetal or adult hemoglobin, inducing γ-globin, stimulating cell differentiation, inhibiting malignant cell proliferation, or treating a hemoglobinopathy or a malignant disease in an subject, comprising an effective amount of an extract from a plant of *Trichosanthes* and a pharmaceutically acceptable carrier.

Further object of the present invention is to provide a use of a plant of *Trichosanthes* in preparing pharmaceuticals for increasing hemoglobin expression level, reactivating fetal or adult hemoglobin, inducing γ-globin, stimulating cell differentiation, inhibiting malignant cell proliferation, or treating a hemoglobinopathy or a malignant disease in an subject, comprising mixing an effective amount of an extract from the plant of *Trichosanthes* with a pharmaceutically acceptable carrier.

Still another object of the present invention is to provide a method for increasing hemoglobin expression level, reactivating fetal or adult hemoglobin, inducing γ-globin, stimulating cell differentiation, inhibiting malignant cell proliferation, or treating a hemoglobinopathy or a malignant disease in an subject, comprising administrating an effective amount of an extract from a plant of *Trichosanthes* to the subject.

In order to obtain an extract from a plant of *Trichosanthes* for achieving one or more of the above-mentioned objects, in one embodiment, the preparation of the extract comprises the steps of:

a) contacting the plant with a first solvent having a polarity index of more than 2.0 to form a mixture;
b) heating the mixture to form a liquor; and
c) concentrating the liquor to form a first syrup having the activity in the subject.

In another embodiment, the preparation further comprises:

d) extracting the first syrup with a second solvent that has a polarity index of less than that of the first solvent to form a second syrup having the activity in the subject.

In a further embodiment; the preparation further comprises:

f) purifying the second syrup thereby obtaining a compound having the activity in the subject.

In a preferred embodiment, the first solvent is preferably selected from the group consisting of water, a lower alkanol and mixtures thereof, more preferably an aqueous solution of about 50-70% ethanol.

In another preferred embodiment, the second solvent is preferably selected from the group consisting of water, a lower alkanol and mixtures thereof, more preferably ethanol.

In still another preferred embodiment, the step b) is performed at a temperature ranging from about 40° to about 80° C., more preferably from about 50° to about 70° C., and most preferably at about 60° C.

Other objects, features and advantages of the present invention will become apparent from the following detailed description when read in conjunction with the accompanying drawings.

BRIEF DESCRIPTION OF THE DRAWINGS

| | |
|---|---|
| Equipment: | Waters ® alliance 2695 separation module |
| Workstation: | Waters ® Millennium[32] chromatography workstation |
| Detector: | PDA 996 Ultraviolet/Visible detector |
| PDA acquisition: | 210-800 nm, 1.2 nm Spectral Resolution, maximum plot |
| Column: | Symmetry ® C4, 4.6 × 250 mm |
| Mobile Phase: | Water 75%, ACN + 0.1% TFA 25% |
| Flow Rate: | 2.0 ml/min |

The single sharp and symmetry peak with the retention time of 7.935 min indicates the lead compound.

DETAILED DESCRIPTION OF THE INVENTION

Definitions

The following definitions are used throughout the application.

As used herein, the term "*Trichosanthes*" denotes any species of the *Trichosanthes* genus. Examples of such plant include, but are not limited to, *Trichosanthes kirilowii* Maxim, *Trichosanthes rosthornii* Harms, and *Trichosanthes japonica* Regel.

As used herein, the term "*Trichosanthes*" also denotes any constituents of the herbal plant. Examples of such constituents include, but are not limited to, roots, stems, leaves, flowers, fruits, and seeds.

As used herein, the term "extract(s)" denotes all possible extracts that are obtained during the sample preparation process and comprise active lead compounds. Examples of such extracts include, but are not limited to, extract A, extract B, and extract C.

As used herein, the term "ingredient(s)" denotes all possible ingredients that are obtained during the sample purification process and comprise active lead compounds. Examples of such ingredients include, but are not limited to, ingredient A, ingredient B, and ingredient C.

As used herein, the term "compound(s)" denotes all possible compounds responsible for the biomedical activity mentioned in this invention. Examples of such compounds include, but are not limited to, the lead compound isolated by HPLC and indicated in FIG. 3, FIG. 4, and FIG. 5.

As used herein, the term "components" denotes all possible extracts, ingredients, and compounds obtained during the sample preparation and purification process.

As used herein, the term "lower alkanol" means an alkyl alcohol having from 1 to 6 carbon atoms. Examples of the lower alkanol include, but are not limited to, methanol, ethanol, n-propanol, iso-propanol, n-butanol, iso-butanol, sec-butanol, and tert-butanol.

As used herein, the term "L" means liters, "mL" means milliliters, "μl" means microliters, "g" means grams, "mg" means milligrams, and "ng" means nanograms; and all temperatures are in degrees Centigrade.

As used herein, the term "globin" refers to any forms of globin. Examples of globin include, but are not limited to, zeta-globin, alpha-globin, epsilon-globin, gamma-globin, delta-globin, and beta-globin.

As used herein, the term "hemoglobin" refers to any forms of hemoglobin. Examples of hemoglobin include, but are not limited to, hemoglobin Gower 1, hemoglobin Gower 2, hemoglobin Porland, fetal hemoglobin (HbF) and adult hemoglobin (HbA) including HbAI and $HbA_2$.

As used herein, the term "hemoglobinopathies" denotes any forms of hemoglobin disorders. Examples of thalassemia include, but are not limited to, alpha-thalassemia, beta-thalassemia, and sickle cell anemia.

As used herein, the term "malignant diseases", denotes a condition characterized by neoplastic, tumorigenic or malignant cell growth. Examples of malignant diseases include, but are not limited to, carcinomas, myelomas, melanomas, lymphomas and leukemias.

As used herein, the term "non-polar solvent(s)" means any organic solvents with a polarity index (Snyder, L. R., 1978, Classification of the solvent properties of common liquids, *J Chromatogr Sci*, 16: 223-34) of not greater than about 2.0, and preferably not greater than about 1.6. Examples of such non-polar solvents include, but are not limited to, hexane, petroleum ether, carbon tetrachloride, and a mixture thereof.

As used herein, the term "polar solvent(s)" means any organic solvents with a polarity index (Snyder, L. R., 1978, Classification of the solvent properties of common liquids, *J Chromatogr Sci*, 16: 223-34) of greater than about 2.0, and preferably greater than about 4.0, and generally easily miscible with water. Examples of such moderately polar solvent include, but are not limited to, methanol, ethanol, acetonitrile, and a mixture thereof.

As used herein, the term "treating" or "treatment" means ameliorating the severity, symptoms or effects of the diseases defined herein.

Natural Products Resources

*Trichosanthes*, also called snakegourd, belongs to Cucurbitaceae family. *Trichosanthes* distribute mainly in tropical and subtropical regions around the world, and some extend even into the temperate zones. The fruit of *Trichosanthes* is a fleshy berry, called *Fructus Trichosanthis*, and with common names of Chinese Cucumber. It also has ethnic names of Gua Lou, Kua Lou, Karo, etc. The other parts of *Trichosanthes* is also called Gua Lou Ren (seed), Gua Lou Pi (fruit pericarp), and Tian Hua Fen (root).

*Trichosanthes* is a kind of Traditional Chinese Herbal Medicine (TCHM) which originated thousands of years ago and was developed by trial and error in China. In legends, the ancient emperors Huangdi and Shennong wrote medical manuals ("Huangdi Neijing"—The Yellow Emperor's Manual on Corporeal Medicine and "Shennong Ben Cao Jing"—Classical Pharmacopoeia of the Heavenly Husbandman) about 5000 years ago. The first record about *Trichosanthes* and its medical application can be found in "Shennong Ben Cao Jing".

According to the traditional Chinese medical manuals, the properties of *Trichosanthes* are sweet and cold. The functions of *Trichosanthes* have been studied for years and it has been clinically used for the treatment of many diseases. For example, *Trichosanthes* helps stimulate the production of body fluids thus relieving dryness. It can disperse phlegm, remove pus, expel toxic matters and is anti-inflammatory. *Trichosanthes* can act as a natural antibiotic, expectorant, laxative, and can be used for abscesses boils bronchitis, constipation, jaundice and hemorrhoids. It has been shown to be excellent for diabetes. The new "AIDS" drug "Compound Q" is a refined protein called trichonanthine which is derived from the *trichosanthes* family.

This invention provides the discovery that *Trichosanthes*, and/or extracts derived thereof, and/or ingredients isolated thereof, and/or compound(s) purified thereof, can positively regulate globin genes expression, and induce the augmentation of adult and fetal hemoglobin level in both human erythroleukemia cell line and normal human hematopoietic progenitor cells.

Active Ingredients Isolation and Single Compound Purification

This invention also relates to methods for extracting, isolating and purifying active ingredients and single compound from *Trichosanthes*.

Accordingly, a first aspect of this invention provides a method for extracting fractions containing active ingredients or compounds from *Trichosanthes* plant tissue. Either water, or organic solvents, or their mixture can be used to prepare the *Trichosanthes* extract.

A second aspect of the invention provides a method for isolating active ingredients from *Trichosanthes*. Fractionally isolated ingredients can be prepared during different purification steps. Examples of such steps include, but are not limited to, rotary evaporation, organic solvents extraction, centrifugation, solid phase extraction, etc.

A third aspect of the invention provides a method for purifying active compounds from *Trichosanthes*. This purification are fulfilled by liquid chromatography, preferably high performance liquid chromatography (HPLC), and eluted with a solvent comprising of water and organic solvents in specific ratio required.

Figure 1:
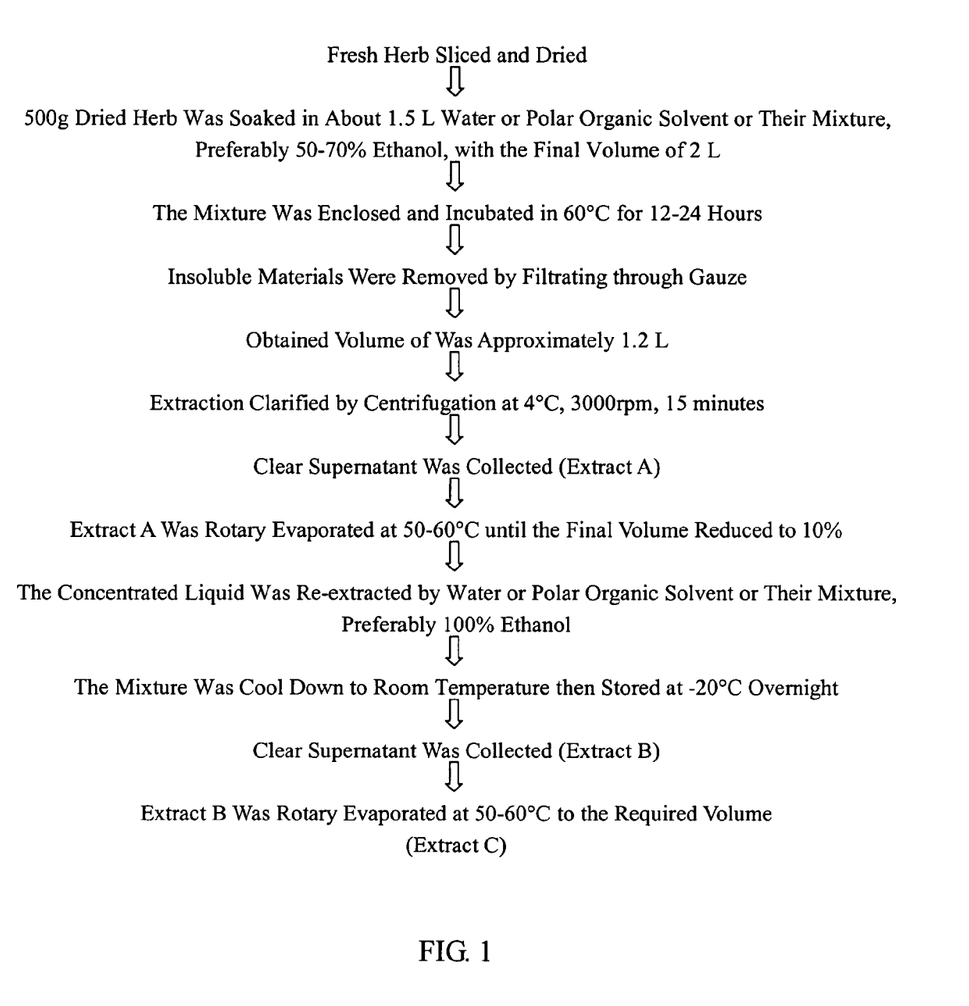
FIG. 1 is a schematic diagram of process steps representative of an embodiment of the present invention in which a mixture of active ingredients is isolated from plant material.

Referring to FIG. 1, the original plant material may be sliced, dried, or physically disintegrated prior to processing. The extraction of herbal plant *Trichosanthes* may be obtained by any methods known in the art, but preferably obtained by soaking the dried plant tissues in water or polar organic solvents or their mixture at any ratio. The resultant mixture should be enclosed and incubated at a certain temperature which usually, but not limited to, ranges from the room temperature to the boiling point of the solvent used. Resulting extract contains biological active ingredients and compounds in its liquid phase. The liquid phase is isolated from the remaining insoluble materials by any means known in the art, but preferably by filtrating through medical gauzes. Remaining insoluble materials may be further removed by centrifugation. The resulting liquid (Extract A) is typically clear and does not require additional filtration, although the skilled technician may go on with further filtration in case necessary.

The previously obtained extract A can be further concentrated into a viscous liquid phase by any means known in the art, preferably by rotary evaporation. The viscous liquid phase is then extracted a second time with a second organic solvent or an organic solvent mixture, the polarity index of which is usually less than that of the first extraction solvent. The extraction methods can be any known one in the art. Examples of the methods include, but are not limited to, strongly vortexing the mixture in a 70° C. water bath when adding a hot extraction solvent continuously, followed by cooling down the solution to room temperature, and then keeping the solution in −20° C. overnight before collecting the supernatant. This polar organic solvent extraction process can be performed once, or repeated several times in case of necessary. The resulting liquid (Extract B) is typically clear and contains biological active ingredients and compounds. The extract B can be concentrated by rotary evaporation if required.

The extraction process can be also performed by other known methods such as counter-current extraction, etc.

Figure 2:
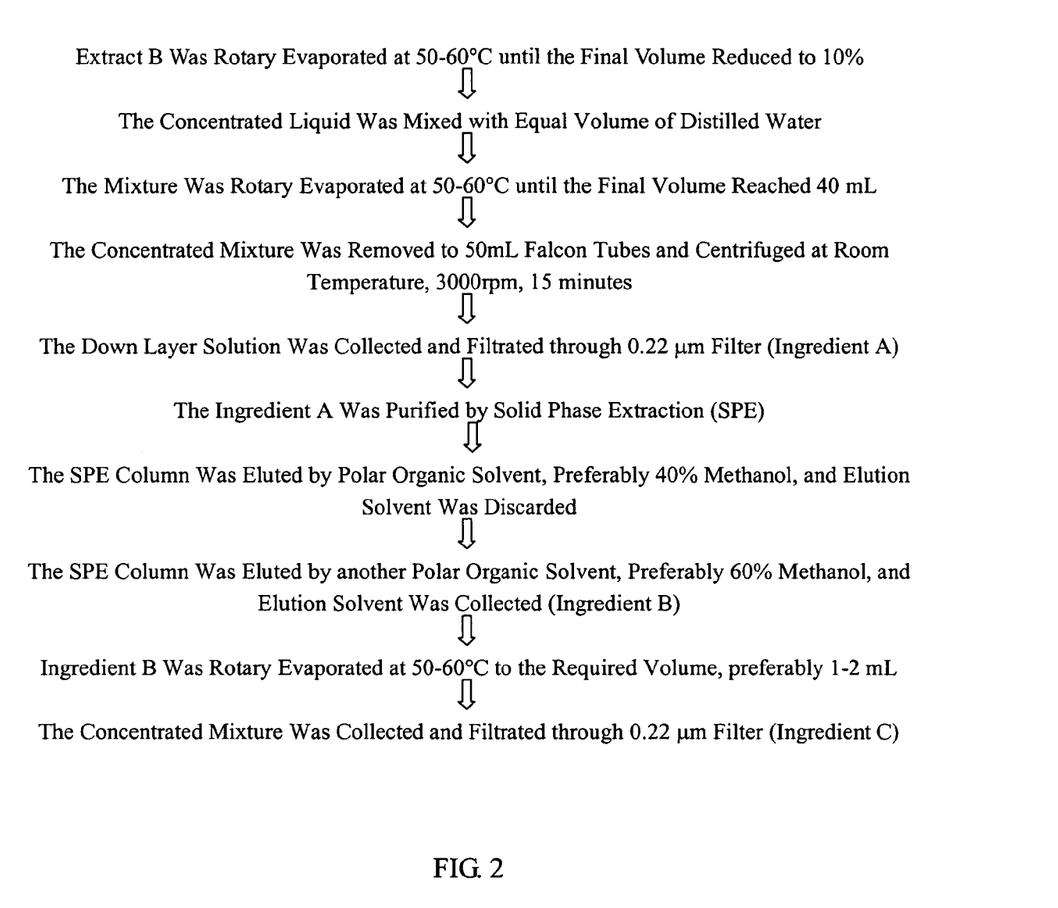
FIG. 2 is a schematic diagram of process steps representative of an embodiment of the present invention in which specific forms of cucurbitane analogs are fractionally isolated from plant material.

Referring to FIG. 2, purified ingredients containing active compounds can be further prepared from Extract B. Extract B is rotary evaporated and the concentrated solvent is mixed with distilled water, preferably with equal volume to the solvent. In one embodiment of the invention, the mixture is further concentrated by rotary evaporation until the final volume reaches about 10% of the original volume. The insoluble materials, comprising lipids, waxes, and pigments, are removed by centrifugation, preferably 3000 rpm for 15 minutes at room temperature. The down layer, comprising a mixture of hydrophilic and moderately polar compounds including the active compounds, is collected and filtrated through 0.22 µm filter (Ingredient A).

Further purified ingredients can be obtained if ingredient A is processed by subsequent separation method. Examples of such method include, but are not limited to, solid phase extraction (SPE), super filtration etc. For SPE, the column is generally eluted by a first polar organic solvent to remove the irrelative ingredients, and then eluted by a second polar organic solvent, usually with less polarity index, to wash out ingredient comprising the active compounds. Finally the second elution solvent is collected (Ingredient B). This ingredient B can be further purified by rotary evaporation and filtrated through 0.22 µm filter (Ingredient C).

Single compound responsible for the biological activity can be isolated by further separation methods. Examples of such methods include, but are not limited to, thin layer chromatography (TLC), gas chromatography (GC), liquid chromatography (LC), and high-performance liquid chromatography (HPLC), of which HPLC is preferred. Different columns can be adopted during HPLC purification. Examples of such columns include, but are not limited to, normal phase columns, reverse phase columns, ion-exchange columns, and size-exclusion columns, of which $C_{18}$ reverse phase columns are preferred.

Figure 3:
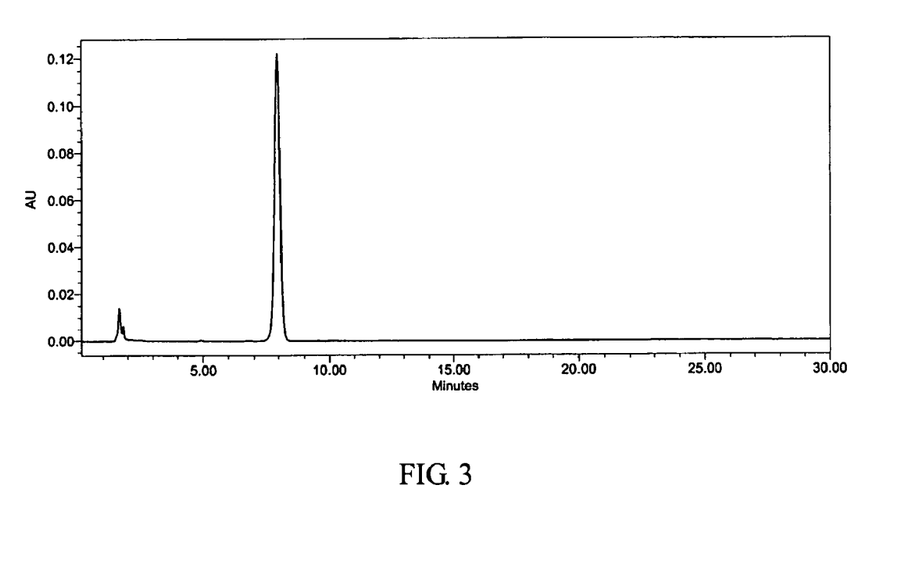
FIG. 3 is a graph representative of an embodiment of the present invention in which a single lead compound is isolated during HPLC purification. Details are as follows.
Figure 4:
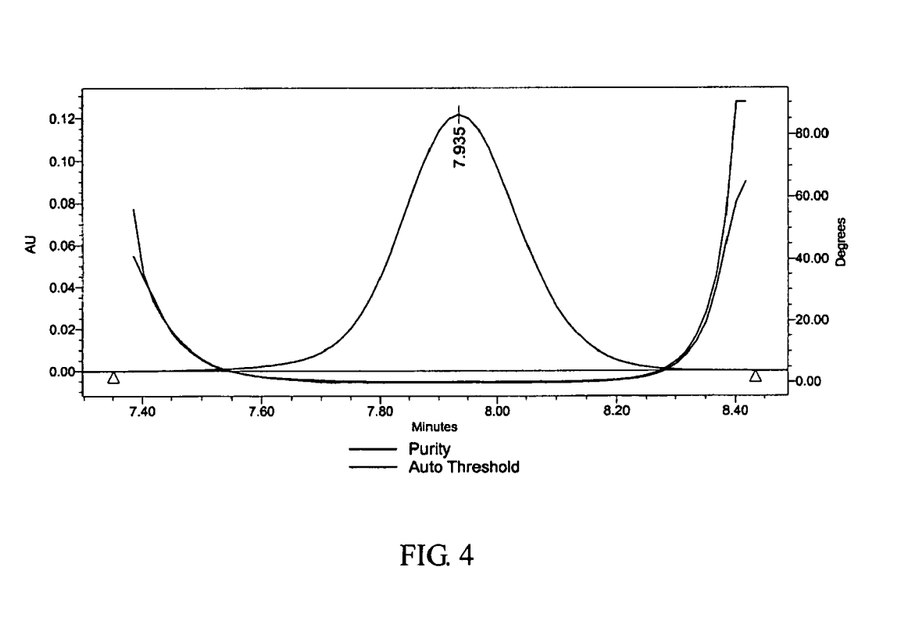
FIG. 4 is a graph representative of an embodiment of the present invention in which the peak purity plot is graphically given out during purification process by Millennium[32] software. The two curves other than base line and peak line are purity angle and purity threshold plot, which is the typical appearance of a homogenous peak with the purity angle (0.076) lower than the purity threshold (0.267).
Figure 5:
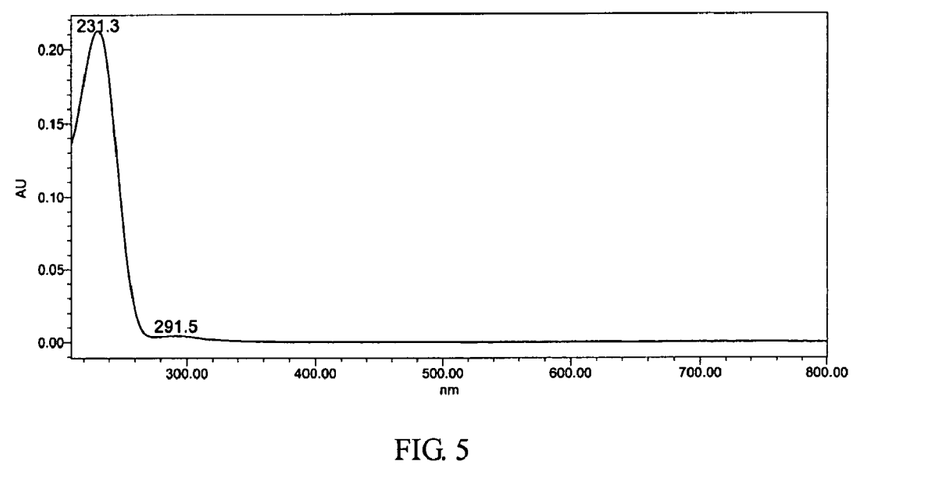
FIG. 5 is a graph representative of an embodiment of the present invention in which the UV/VIS spectrum is graphically given out during purification process PDA 996 detector. Two absorbance peaks can be identified, of which the maximum absorbance appears at 231.3 nm.

In one embodiment of the invention, the active compound is purified by reverse phase $C_{18}$ HPLC, using gradient elution protocol, from 0% to 60% methanol. The resulting product will comprise active compound in essentially pure form. However, the purity can be raised if the HPLC purification process is repeated. FIG. 3 provides an example of the pure active compound derived from HPLC separation, the purity plot (from Waters® Millennium[32] software) of which is indicated in FIG. 4. FIG. 5 provides an example of the ultraviolet/visible spectrum of the pure active compound derived from the photodiode array (PDA) detector from HPLC separation module (Waters® alliances® 2695/PDA 996). To get the powder form of the compound, the collected solution should be rotary evaporated followed by frozen and lyophilized.

The skilled technician will appreciate that solvents, separation methods, and elution methods not explicitly recited in the foregoing may be successfully utilized in the practice of the present invention, and that these alternate materials and methods may be determined without undue experimentation.

Biomedical Applications

This invention encompasses any components derived from the above extracts, ingredients or compounds. According to one embodiment, the invention provides a pharmaceutical composition comprising components of extract A, extract B, extract C, ingredient A, ingredient B, ingredient C, or purified lead compound in an amount effective to increase the production of fetal hemoglobin or stimulate cell differentiation in a patient and a pharmaceutically acceptable carrier or adjuvant. More specifically, these compositions are designed to treat a patient suffering from a hemoglobinopathy or a malignant disease.

In a preferred embodiment, these compositions additionally comprise a conventional agent used in the treatment of hemoglobinopathies. The conventional agent may be present in the same amount or less than that normally required to treat hemoglobinopathies in a monotherapy. The normal dosages of these conventional agents are well known in the art. Such agents include hydroxyurea, recombinant human erythropoietin, short-chain fatty acid derivatives which include, but not limited to, phenylacetic acid, phenylbutyric acid, and valproic acid. Preferably, the conventional agent used is hydroxyurea.

In an alternate preferred embodiment, the compositions additionally comprise a conventional agent used in the treatment of diseases characterized by neoplastic, tumorigenic, malignant cell growth, or other hematological disorders in a patient. This additional agent may be present in an amount equal to or less than that normally required to treat such diseases in a monotherapy.

The carriers and adjuvants in the composition of this invention include, for example, ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes such as protamine sulfate, disodium hydrogen phosphate, sodium chloride, zinc salts, colloidal silica, magnesium, trisilicate, polyvinyl pyrrolidone, cellulose-based substances and polyethylene glycol. Adjuvants for topical or gel base forms may be selected from the group consisting of sodium carboxymethylcellulose, polyacrylates, polyoxyethylene-polyoxypropylene-block polymers, polyethylene glycol and wood wax alcohols.

Generally, the pharmaceutical compositions of this invention may be formulated and administered to the patient using methods and compositions similar to those employed for other pharmaceutically important agents. Any pharmaceutically acceptable dosage route, including, oral, topical, intranasal, or parenteral (including intravenous, intramuscular, subcutaneous, intracutaneous, periosteally, intra-articular, intrasynovial, intrathecal, intrastemal, intracranial or intralesional) may be used.

The pharmaceutical compositions of this invention may be provided in a variety of conventional depot forms. These include, for example, solid, semi-solid and liquid dosage forms, such as tablets, pills, powders liquid solutions, dilutions, suspensions, emulsions, liposomes, capsules, suppositories, injectable and infusible solutions. The preferred form depends upon the intended mode of administration and therapeutic application.

For example, oral administration of the pharmaceutical compositions of this invention may be any orally acceptable dosage forms including, but not limited to, capsules, tablets, and aqueous or non-aqueous suspensions, emulsions, oil dilutions and solutions. In the case of tablets for oral use, carriers which are commonly used include lactose and corn starch. Lubricating agents, such as magnesium stearate, are also typically added. For oral administration in a hard gelatin capsule form, useful diluents include lactose and dried corn starch. Soft gelatin capsules incorporating oils and/or polyethylene glycols excipients may also be used. When aqueous suspensions or emulsions are administered orally, the pharmaceutical compositions are combined with emulsifying and suspending agents. Flavoring, sweetening, or coloring agents may be added, if desired.

The hemoglobinopathies which may be treated by components from this invention include sickle cell syndromes, such as sickle cell anemia, hemoglobin SC disease, hemoglobin SS disease and sickle beta-thalassemia; thalassemia syndromes, such as beta-thalassemia and alpha-thalassemia; other genetic mutations of the globin gene locus that lead to unstable hemoglobins, such as congenital Heinz body anemia, globin mutants with abnormal oxygen affinity and structural mutants of globin that result in thalassemic phenotype.

According to a preferred embodiment, the above-described method comprises the additional step of treating the patient with an agent that is normally used to treat such hemoglobinopathies, e.g., hydroxyurea. That agent may be administered prior to, sequentially with or after treatment with the cucurbitane analog-containing composition. Of course, if the composition used to treat the disease is one that already contains such conventional agent, this additional step can be omitted.

According to another embodiment, the invention provides method for treating diseases characterized by neoplastic, tumorigenic or malignant cell growth, or malignant hematological disorders. Treatment includes prevention of the progression the disease or its recurrence. Such diseases include carcinomas, myelomas, melanomas, lymphomas and leukemias. Preferably, the method provides the same or higher serum ingredient/compound concentrations indicated above as being desirable for treating hemoglobinopathies.

According to a preferred embodiment, the above-described method comprises the additional step of treating the patient with an agent that is normally used to such malignancies. That agent may be administered prior to, sequentially with or after treatment with the lead compound-containing composition. Of course, if the composition used to treat the disease is one that already contains such conventional agent, this additional step can be omitted.

Combination therapies with conventional agents according to this invention may also exert an additive or synergistic effect, particularly when each component acts to treat or prevent the target disease via a different mechanism.

In order that the invention described herein may be more fully understood, the following examples are set forth. It should be understood that these examples are set forth for illustrative purposes only and are not to be construed as limiting this invention in any manner.

EXAMPLE 1

Extraction and Purification of Active Components from Traditional Chinese Herbal Medicine—Fructus Trichosanthis Fructus Trichosanthis were collected, dried and pulverized. Total 500 g herb was removed to a 2L bottle and 70% ethanol was added to soak up all materials inside with the final volume up to 2000 mL. The resulting solution was enclosed and incubated in 60° C. for 24 hours. The inside ethanol was then removed for rotary evaporation after simple percolation. The remained herb could be extracted once more before being discarded. The rotary evaporation was operated at 60° C. until finally the inner mixture became viscous liquid, when the final volume was about 100 mL. The concentrated extract was removed to another 2L bottle.

The whole extraction steps were repeated for 4 times and the final volume of collected extract reached to about 400 mL.

Concentrated herb extract was incubated in boiling water for 15 min, while preparing another 1500 mL absolute ethanol in 70° C. water bath at the same time. Then the hot ethanol was added to the herb extract slowly, and the mixture was strongly vortexed simultaneously. The mixture was cooled down at the room temperature and further stored in −20° C. overnight.

The supernatant was collected from the mixture and rotarily evaporated until 200 mL solution was left. Then the solution was added to 200 mL distilled water, and followed by vacuum evaporation until the final volume of the solution reached 100 mL. The concentrated mixture was moved to 50 mL Falcon tubes and centrifuged in 300 rpm for 15 min at the room temperature. The down layer solution was collected and filtrated through 0.22 µm filter.

The collected down layer solution was added to a $C_{18}$ SPE column (Oasis® HLB, Waters). And then the following steps were performed: 1) eluting the column with 40% methanol and collect the elution as solution A; 2) eluting the column with 60% methanol and collecting the elution buffer as solution B; 3) eluting the column with 100% ethanol and discarding the elution buffer; 4) eluting the column with 100% water and discarding the elution; 5) repeating the protocol for 3-5 times using solution A as the initial sample; and 6) collecting all the solution B and vacuum evaporating it to 1 mL and discarding all thus produced sedimentation by filtration across 0.22 µm filter.

A Nova-Pak $C_{18}$ reverse phase column (7.8×300, Waters) was adopted for further HPLC (Waters 2695 separation module with PDA 996 detector) purification. The injected sample was eluted with water/methanol with a linear gradient from 0% to 60% (the percentage of methanol) in 30 min at a flow rate of 3.0 mL/min. The lead compound yielding was 0.3 mg.

The peak of the lead compound was identified in FIG. 3. The single sharp and symmetry peak indicated the LC978 with the retention time of 7.935 min. Peak purity plot was graphically given out during peak analysis by Millennium$^{32}$ software and was indicated in FIG. 4. The retention time of the peak was 7.935 min. The two lines other than base line and peak line were purity angle and purity threshold plot. It was the typical appearance of a homogenous peak that the purity angle (0.076) line was lower than the purity threshold (0.267) line. The UV/VIS Spectrum of the lead compound was shown in FIG. 5. The scanning wavelength range was from 210 nm to 800 nm. Two absorbance peaks were identified, of which the maximum absorbance was at 231.3 nm.

EXAMPLE 2

Large-Scale Extraction and Purification of Active Components from *Trichosanthes*

Herbal medicine *Trichosanthes* were collected, dried and pulverized. Total 200 kg herb was removed to a 1000L container, to which distill water was added until all herbal materials were soaked. The resulting solution was enclosed and incubated in 100° C. for 3 hours with continuous stirring. The liquid extract was then collected, clarified, and concentrated to 20% volume by rotary evaporation. The concentrated extract was removed to another container.

Then the concentrated herb extract was heated to 60° C. 2 volumes of hot ethanol were added into the herb extract slowly, and the mixture was strongly stirred simultaneously. After sufficient vortex, the mixture was cooled down to room temperature. The supernatant was collected and concentrated by rotary evaporation.

The concentrated materials were re-extracted by 10L ethanol absolute at room temperature with strong stirring. The supernatant was collected and concentrated by rotary evaporation. The re-extraction process was repeated for one more times and the concentrated solution was finally resolved in 40% methanol. This solution was further purified by SPE and HPLC. Preparative column was used in HPLC purification and the injected sample was eluted with water/acetonitrile with a linear gradient from 0% to 20% (the percentage of acetonitrile) in 30 min. The lead compound yielding was 120 mg.

EXAMPLE 3

*Trichosanthes* Components Induced Hemoglobin Expression on K562 Cell Line

The K562 cell line is considered to be a multipotent hematopoietic stem cell because it has multiple-lineage markers. The cells could be induced to erythrocytic, monocytic, granulocytic and megakariocytic differentiation using various materials. Since its discovery, K562 cell line has been extensively used as a model in studies of erythroid differentiation and regulation of globin gene expression.

K562 cells (ATCC) were cultured in RPMI 1640 (Gibco) supplemented with 10% fetal calf serum (FCS, Gibco) and 1% PSN (Gibco). The cultures were maintained under a humidified atmosphere with 95% air/5% $CO_2$ at 37° C.

The hemoglobin positive K562 cells can be identified by 3,3',5,5'-tetramethylbenzidine (TMB, Sigma) staining. In brief, 10 μl/cell suspension was pipetted out and mixed with 10 μl TMB working solution. Five minutes later, cells were scored as positive (blue) or negative (pale yellow) at 200× microscope.

Before the assay, K562 cells were scored first by TMB staining to ensure there was no selfdifferentiation (TMB positive cell percentage less than 1.0%). 100 μl/well complete RPMI 1640 was added into a 96-well plate, and 180 μl was added in the first well. 20 μl *Trichosanthes* extraction components was added into the first well immediately. Then 100 μl of the mixture was transferred to the next well. By such one half dilution method, serial dilutions of *Trichosanthes* extraction components were got.

100 μl K562 cell suspension with the density of 4×10$^4$ cells/ml was add into each well of the 96-well plate. The final cell suspension was mixed well and cultured in the 37° C. $CO_2$ incubator with certain humidity for six days. Then the hemoglobin positive cells were recorded by TMB staining.

The results showed that the lead compound from *Trichosanthes*, as well as any extract or ingredient containing this lead compound, can significantly induce erythrocytic differentiation and hemoglobin expression. Table 1 showed a summary of the observations.

TABLE 1

Positive Cell Percentage of Different Treated K562 Cells

| Componets | TMB Positive Cell Percentage | Components | TMB Positive Cell Percentage |
|---|---|---|---|
| Negative Control | 10.3 ± 1.5 | Ingredient A | 63.1 ± 3.7 |
| Hydroxyurea | 66.7 ± 4.4 | Ingredient B | 61.9 ± 4.8 |
| Extract A | 56.8 ± 3.9 | Ingredient C | 66.5 ± 3.6 |
| Extract B | 58.6 ± 5.1 | Lead Compound | 68.7 ± 4.1 |
| Extract C | 58.1 ± 4.4 | | |

Note:
The dosage of hydroxyurea (positive control) is 25.0 μg/ml.
The TMB positive percentage refers to the group of cells that treated with optimal dosage of Trichosanthes extraction components and showed maximal positive cell percentage.

EXAMPLE 4

Dose-Response Effect of the Lead Compound

Dose-response effect of the lead compound from *Trichosanthes* was studied on K562 cells which were cultured and assayed as described in example 3. In brief, K562 cell suspension was mixed with serial two-fold diluted medium containing the lead compound and cultured for six days. Then the hemoglobin positive cells were recorded by TMB staining.

Figure 6:
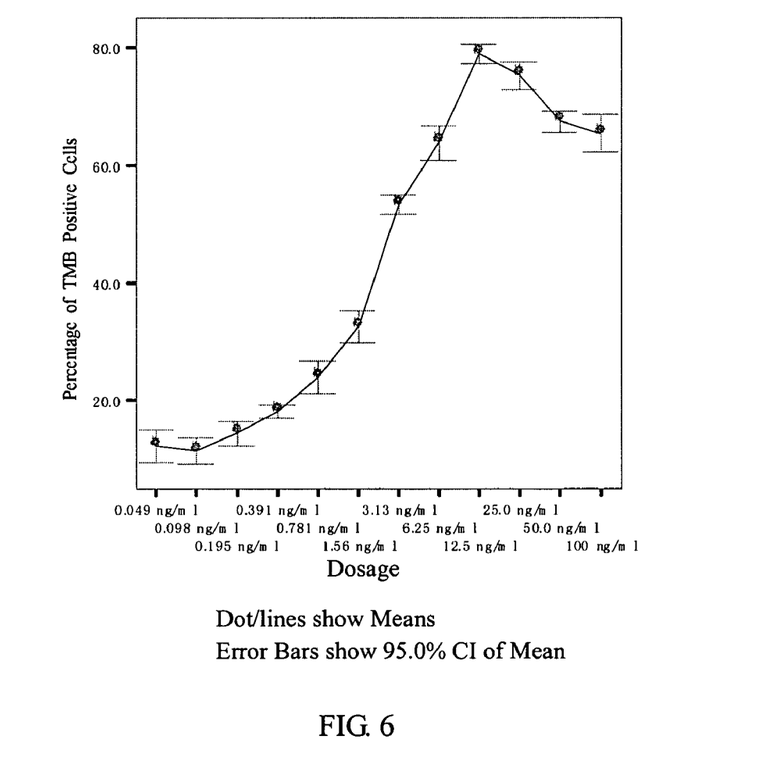
FIG. 6 is a graph representative of an embodiment of the present invention in which the dose-response curve of the lead compound on K562 Cell Line is graphically plotted. The curve indicates the optimal dosage of the lead compound for K562 cells is 12.5 ng/ml and it also brings the direct evidence that the hemoglobin inducing activity is relevant to the lead compound.

As shown in FIG. 6, the optimal dosage of the lead compound for K562 cells is 12.5 ng/ml. Lower dosage brings decreased effect, and no activity can be detected for the dosage lower than 0.1 ng/ml. On the contrary, higher dosage also brings decreased activity, which could be due to the cytotoxic effect of the lead compound. However, this cytotoxic effect is of potential practical use in antitumor area. The dose-response curve provided the direct evidence that the hemoglobin inducing activity is relevant to the lead compound.

EXAMPLE 5

FACS Analysis of K562 Cells Treated by Different Compounds

K562 cells were cultured with hydroxyurea (HU, 25 mg/ml) and the lead compound from *Trichosanthes* (12.5 ng/ml) for 6 days. Then the cells were conjugated with PE labeled mouse anti human fetal hemoglobin monoclonal antibodies (Becton Dickinson) followed by FACS analysis. In brief, 1×10$^6$ cells were collected in a 15 ml falcon tube and centrifuged in 150 rpm for 5 min. The cell pallet was washed with PBS. Then cells were fixed by gently mixing with 1 ml PBS with 4% formaldehyde (37-40%, Merck) for 1 hr at room temperature. The fixed cells were washed once with PBS and then were resuspended in 100 μl 0.01% Triton X-100 (Merck) in PBS/0.1% BSA (Sigma). 20 μl monoclonal antibody was added in, followed by mixing thoroughly and incubating for 30 min in darkness at room temperature, with frequent gentle shaking. Finally the cells were washed with 1× PBS with 0.1% sodium azide once and kept in 4° C. until analysis.

Figure 7:
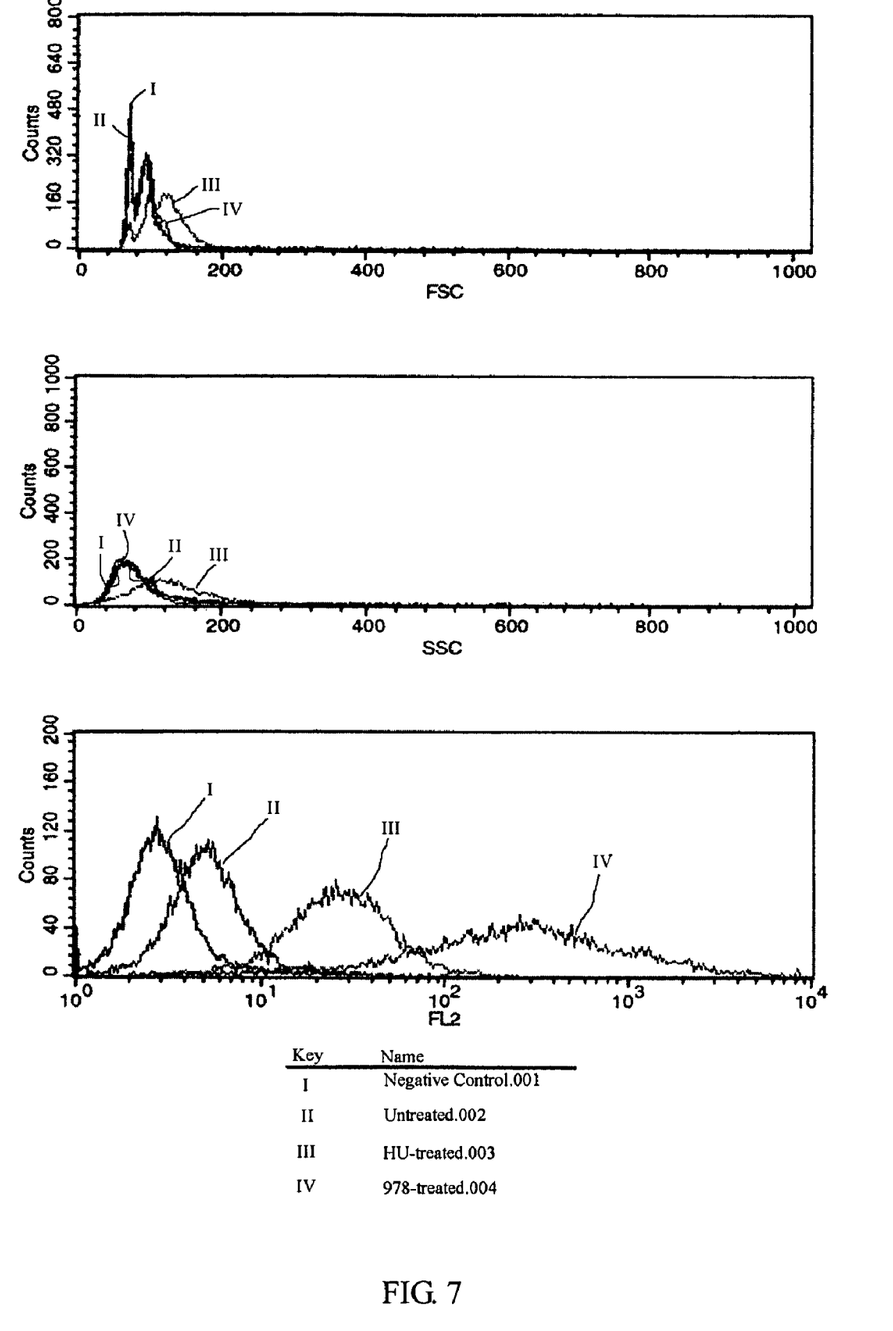
FIG. 7 is a graph representative of an embodiment of the present invention in which the fetal hemoglobin expression of K562 cells treated by different compound was analyzed by flow cytometer. K562 cells were cultured for 6 days with hydroxyurea (HU, 25 mg/ml) and lead compound from *Trichosanthes* (namely 978, 12.5 ng/ml). Then the cells were conjugated with PE labeled mouse anti human fetal hemoglobin monoclonal antibodies followed by FACS analysis. Expression of fetal hemoglobin is induced in both compound treated K562 cells, but more significantly in the cells treated by lead compound from *Trichosanthes*. The results also provide the fact that the lead compound from *Trichosanthes* can positively induce not only adult hemoglobin, but also fetal hemoglobin expression.

As shown in FIG. 7, from FSC and SSC, K562 cells treated by the lead compound showed no obvious cell morphology changes, comparing with negative control and untreated cells. However, there existed obvious morphology changes in HU-treated cells. This could be due to the cytotoxicity of hydroxyurea in such high dosage. Expression of fetal hemoglobin was induced in both compound treated cells, but more significantly in the lead compound treated cells. The results also provided the fact that the lead compound from *Trichosanthes* can positively induce not only adult hemoglobin, but also fetal hemoglobin expression.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of examples.

What is claimed is:

1. A pharmaceutical composition comprising an extract from *Trichosanthes rosthornii Harms* or *Trichosanthes japonica Regal*, wherein said extract is prepared by a method comprising the steps of:

(a) contacting *Trichosanthes rosthornii Harms* or *Trichosanthes japonica Regal* with a first solvent consisting of an aqueous solution of from 50% to 70% ethanol to form a mixture;
(b) heating the mixture to form a liquor; and
(c) concentrating the liquor to form a first syrup.

2. The pharmaceutical composition of claim 1, wherein said method further comprises the step of:
(d) extracting the first syrup with a second solvent having a polarity index less than that of the first solvent to form a second syrup.

3. The pharmaceutical composition of claim 2, wherein said method further comprises the step of:
(e) purifying the second syrup.

4. The pharmaceutical composition of any one of claims 1-3, wherein the extract exhibits a major peak with a retention time of 7.935 min when analyzed by high performance liquid chromatography using a 4.6×250 mm C4 column, a mobile phase with 75% water and 25% acetonitrile/0.1% trifluoroacetic acid, at a flow rate of 2.0 ml/min.

5. The pharmaceutical composition of any one of claims 1-3, wherein the extract is prepared from the roots, stems, leaves, flowers, fruits, or seeds of *Trichosanthes rosthornii Harms* or *Trichosanthes japonica Regal*.

6. The pharmaceutical composition of any one of claims 1-3, further comprising a pharmaceutically acceptable carrier or adjuvant.

7. The pharmaceutical composition of any one of claims 2 and 3, wherein the second solvent is a lower alkanol, or a mixture of water and a lower alkanol.

8. The pharmaceutical composition of claim 2, wherein the second solvent is ethanol.

9. The pharmaceutical composition of claim 1, wherein step (b) is performed at a temperature ranging from 40° C. to 80° C.

10. A method of preparing an extract from a plant of *Trichosanthes* for manufacturing a pharmaceutical composition, comprising the steps of:
(a) contacting the plant with a first solvent consisting of an aqueous solution of from 50% to 70% ethanol to form a mixture;
(b) heating the mixture to form a liquor;
(c) concentrating the liquor to form a first syrup; and
(d) extracting the first syrup with a second solvent having a polarity index less than that of the first solvent to form a second syrup.

11. The method of claim 10, wherein the extract exhibits a major peak with a retention time of 7.935 min when analyzed by high performance liquid chromatography using a 4.6×250 mm C4 column, a mobile phase with 75% water and 25% acetonitrile/0.1% trifluoroacetic acid, at a flow rate of 2.0 ml/min.

12. The method of claim 10 or 11, wherein the plant is *Trichosanthes kirilowii Maxim, Trichosanthes rosthornii Harms* or *Trichosanthes japonica Regal*.

13. The method of claim 10 or 11, wherein the extract is prepared from the roots, stems, leaves, flowers, fruits, or seeds of the plant.

14. The method of claim 10 or 11, wherein the pharmaceutical composition further comprises a pharmaceutically acceptable carrier or adjuvant.

15. The method of claim 10 or 11, wherein the second solvent is a lower alkanol, or a mixture of water and a lower alkanol.

16. The method of claim 10 or 11, wherein the second solvent is ethanol.

17. The method of claim 10 or 11, wherein step (b) is performed at a temperature ranging from 40° C. to 80° C.

\* \* \* \* \*